United States Patent
Shanbrom

[11] Patent Number: 5,814,225
[45] Date of Patent: Sep. 29, 1998

[54] IODINATED GEL FILTRATION MEDIA FOR DISINFECTING PROTEIN SOLUTIONS

[75] Inventor: Edward Shanbrom, Santa Ana, Calif.

[73] Assignee: Shanbrom Technologies LLC, Ojai, Calif.

[21] Appl. No.: 667,448

[22] Filed: Jun. 21, 1996

Related U.S. Application Data

[63] Continuation-in-part of Ser. No. 562,795, Nov. 27, 1995, abandoned, which is a continuation of Ser. No. 255,616, Jun. 9, 1994, abandoned.

[51] Int. Cl.$^6$ .................................................. B01D 15/08
[52] U.S. Cl. ........................ 210/656; 210/767; 210/638; 210/753; 210/658; 210/198.2; 210/501
[58] Field of Search ................................ 210/638, 198.2, 210/501, 658, 753, 656, 767

[56] References Cited

U.S. PATENT DOCUMENTS

| | | |
|---|---|---|
| 4,010,259 | 3/1977 | Johansson . |
| 4,460,642 | 7/1984 | Errede et al. ............................ 428/283 |
| 4,575,484 | 3/1986 | Straus ............................................ 435/7 |
| 4,783,448 | 11/1988 | Johansson ................................. 514/57 |
| 4,946,673 | 8/1990 | Pollack et al. ............................. 424/80 |
| 5,360,605 | 11/1994 | Shanbrom ............................... 424/667 |
| 5,370,869 | 12/1994 | Shanbrom ................................. 424/78 |

*Primary Examiner*—Ana Fortuna
*Attorney, Agent, or Firm*—Stefan J. Kirchanski

[57] ABSTRACT

A process for disinfecting protein solutions operates by flowing the solutions through a bed of iodinated organic polymer that acts as a gel filtration material. The preferred types of gel filtration material is Sephadex brand cross-linked dextrans, either G-25 or A-25 (DEAE modified Sephadex). The various types of cross-linked dextrans are readily iodinated before use by being mixed dry with elemental iodine at an elevated temperature such as 37° C. Sephadex brand cross-linked dextrans can be readily iodinated to 50% weight of iodine to weight of dextrans or more. The preferred level of iodination is 30–40%. Before use the used it is first swelled in aqueous medium and then poured into a chromatographic column. Six ml of swelled 30% iodine Sephadex A-25 can effectively destroy virus in at least one liter of 5% human IgG.

12 Claims, 2 Drawing Sheets

PLACE SEPHADEX INTO CAPPED CENTRIFUGE TUBE

ADD SOLID IODINE TO CENTRIFUGE TUBE

SEAL CENTRIFUGE TUBE AND AGITATE TUBE AT 37°C

IODINATED GEL FILTRATION MEDIA FOR DISINFECTING PROTEIN SOLUTIONS

The present application is a continuation in part of earlier U.S. patent application Ser. No. 08/562,795, filed Nov. 27, 1995, abandoned, which, in turn, was a continuation of earlier U.S. patent application Ser. No. 08/255,616, filed Jun. 9, 1994, now abandoned.

BACKGROUND OF THE INVENTION

1. Field of the Invention

The current invention concerns the use of iodine as a disinfectant substance and, more particularly, a method of treating polymeric gels used in gel filtration chromatography with iodine to create a novel disinfectant substance.

2. Description of Related Art

The use of iodine as an aerial disinfectant has been advocated at least since 1926, and experiments on the disinfection of air have been carried out, mainly during World War II. Aerial disinfection of air-raid shelters with iodine vapors as a prophylactic measure against influenza has been recommended and a "relatively tolerable" concentration of 0.1 mg/ft$^3$ (3.5 mg/ml) was found to be sufficient for a rapid kill of freshly sprayed salivary organisms.

Iodine is used widely in human medicine in the disinfection of skin (e.g., the preoperative preparations of the skin, the surgical disinfection of hands, the disinfection of the perineum prior to delivery, and the disinfection of the skin prior to transfusions). Iodine preparations are also used for therapeutic purposes, e.g. the treatment of infected and burned skin, but iodine is a strong irritant unless combined with an iodophor. Iodine has also been used for the disinfection of medical equipment, such as catgut, catheters, knife blades, ampoules, plastic items, rubber goods, brushes, multiple-dose vials, and thermometers.

Various authors have tried to summarize the disinfecting properties of iodine and the other halogens by reviewing the literature and analyzing the existing data. One of the major uses of iodine has been in disinfecting drinking water. According to the literature, on a weight basis, iodine can inactivate viruses more completely over a wide range of water quality than other halogens. In the presence of organic and inorganic nitrogenous substances, iodine is the cysticide of choice because it takes part in fewer side reactions that consume the disinfectant before it can act. Gottardi, W., *Iodine and Iodine Compounds in Disinfection, Sterilization, and Preservation* 3d Ed., Block, Seymour S., Ed., Lea & Febiger, Philadelphia (1983). The references cited therein provide more details respecting the background discussed above.

The present inventor has long worked on using iodine to disinfect blood and various fractions and components derived therefrom. For additional information the reader is referred to U.S. Pat. Nos. 5,360,605, and 5,370,869 by the present inventor which are incorporated herein by reference. One of the vexing problems has been the difficulty of effectively disinfecting clotting factors and other blood-derived proteins with iodine. When sufficient iodine to ensure kill of all known pathogens is applied, many of the proteins prove labile and are denatured.

The present inventor has found that donating active iodine from a solid iodine carrier rather than adding iodine as a solute is more effective in destroying pathogens while limiting the denaturation of important proteins. For example, a bed of iodinated insoluble polyvinyl pyrollidone (an iodophor) has been found a useful means for disinfecting various solutions containing proteins and/or cells or cellular components. It has also been found that it is advantageous to limit the extent of the added iodine's action by either removing the iodine (e.g., by addition of an iodine binding material) or by neutralization of the iodine (e.g., by addition of an effective reducing agent). Despite these improvements an ideal means of applying disinfecting iodine to blood, blood fractions and similar protein-containing solutions is still needed.

OBJECTS AND SUMMARY OF THE INVENTION

It is an object of the present invention to provide a simple and reliable method and composition of matter for applying disinfecting iodine to blood, components purified from blood, and protein solutions;

It is an additional object of the present invention of providing a reliable, commercially available iodine disinfecting material for use on blood, components purified from blood, and protein solutions;; and It is a further object of the present invention to provide a reliable iodine disinfecting material that can destroy a range of viruses and other pathogens without destroying the blood, components purified from blood, or protein solutions; that are being disinfected.

These and additional objects are met by a process in which protein solutions to be disinfected are allowed to flow through a bed of iodinated gel filtration material. The preferred types of gel filtration material is Sephadex®, either G-25 or A-25 (DEAE modified Sephadex). The various types of Sephadex are readily iodinated before use by being mixed dry with elemental iodine at an elevated temperature such as 37° C. Sephadex can be readily iodinated to 50% weight of iodine to weight of Sephadex or more. The preferred level of iodination is 30–40%. Before use the Sephadex® is swelled in aqueous medium and then poured into a chromatographic column. Six ml of swelled 30% iodine Sephadex can effectively destroy virus in at least one liter of 5% human IgG.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
FIG. 1 represents a flow diagram of the process of making the iodinated gel filtration medium of the present invention.
Figure 1:

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a method of producing and using an iodinated organic polymeric gel filtration material for use as a disinfectant of protein solutions.

Plastics and various related organic polymers can be iodinated by maintaining them in an iodine vapor-containing environment for a suitable period of time. The amount of time of such exposure is a function of (a) the amount of iodine desired in the treated material, (b) the permeability of the material, and (c) the vapor pressure of iodine in the environment.

Vapor pressure is a function of temperature in accordance with the Antoine equation (see any standard chemical handbook, e.g. *Lang's Handbook of Chemistry*, John A. Dean, Ed., 14th edition, McGraw-Hill, Inc., New York). Table 1 provides sufficient information as to temperature-vapor pressure relationships for processes contemplated by this invention.

TABLE 1

Iodine Vapor Pressure

| Temperature Deg. C. | Vapor Pressure mm Hg. |
| --- | --- |
| 0 | >1 |
| 20 | ~2 |
| 40 | 3 |
| 60 | 13 |
| 80 | 39 |
| 100 | 108 |
| 120 | 268 |
| 140 | 612 |

The vapor pressure at any desired temperature is easily calculated if desired; however, simple experimentation has been found to be more satisfactory than calculations because, it is believed, of the great variability in permeability and rate of permeation of various organic polymers.

The rate of permeation of organic polymers is a function of temperature, permeability increasing with temperature; however, there is no known theoretical or empirical method of predicting iodine permeability for polymers in general. As to a given material, however, simple experimentation permits quick and easy establishment of vapor phase treatment parameters. It will be seen from Table 1 that high iodine vapor pressures can be obtained at temperatures well below the degradation temperature of nearly all organic polymers.

The above discussion of iodine vapor pressure and permeability of organic polymers is of particular importance because "beads" made of various organic polymers are widely used as chromatographic agents in biochemical purification. Of particular interest are those materials used in "protein exclusion" or gel filtration chromatography. These materials are generally used as "beads" of organic polymer in their hydrated form (cross-linked polyacrylamide and cross-linked glucose polymer (dextrans) are popular although other organic polymers with similar properties are also suitable). When these gels are hydrated, the polymer swells by imbibing water, but the covalent cross-links in the polymer structure limit the size of water-filled pores within the hydrated gel. These pores then behave like pores in dialysis membrane and admit or exclude solutes of different sizes depending on the pore size. If the pores are small, water and simple solutes can penetrate into the matrix of the beads, but larger solutes molecules like proteins are excluded. If protein solutions are poured through such a bed of hydrated beads, the proteins rapidly pass through, whereas other smaller solutes within the solution enter the beads and are retarded in their passage through the bed. This allows one to remove small solutes from proteins. If larger pores are present, the beads admit smaller, but not larger, proteins so that protein mixtures can be fractionated and purified.

If gel filtration materials are loaded up with iodine, one can produce a controlled iodine source. As blood and blood components are passed through a bed of such a material, iodine constantly migrates to the surface of the beads (through the water-filled pores) and is donated to the passing fluid. However, the labile proteins are unable to penetrate the gel (the pores are too small) and, hence, are prevented from contacting the large concentration of iodine within the beads. In this way a controlled amount of disinfecting iodine is metered out to the solution allowing disinfection while sparing the labile proteins in the solution.

While any of the large number of gel chromatography materials are applicable to the present invention, the polymerized, cross-linked dextrans (glucose polymers) gels known as "SEPHADEX®" produced by Pharmacia-Upjohn are especially preferred. There are a wide range of these Sephadex products wherein a number is added to the product name to refer to the molecular weight of proteins that are excluded by the gel (i.e., an indication of the pore size of the cross-linked polymer). Larger numbers indicate more open gels with larger pores. The more open the gel, the more the beads tend to deform and slow the rate of liquid flow therethrough. If a Sephadex® with too large a pore size is used, important proteins may penetrate the gel and become over-iodinated. Also, since the overall flow is slower, dwell time of the protein within the bead bed is extended also favoring over-iodination. Materials with either a "25" or a "50" rating (i.e., gel excludes proteins >25 or 50 kilodalton molecular weight, respectively) are appropriate in that either material excludes important blood proteins. However, flow rate is about ten times greater in the "25" material causing this material to be greatly preferred.

The simplest form of Sephadex is known as "G" type Sephadex® (i.e., Sephadex® G-25 or G-50). Other types of Sephadex are available in which the cross-linked polymer has been derivatized with various chemical groups to provide additional properties, such as ion exchange, to the polymer. DEAE (diethyl aminoethyl) Sephadex is a popular anion exchanging Sephadex derivative. It appears that DEAE Sephadex® is somewhat more effective as an iodine donor than unmodified Sephadex. This may be due to the DEAE's ability to bind iodide ions; a locally high concentration of iodide ions may help render the absorbed iodine more readily soluble (as in Lugol's solution which consists of iodine plus iodide), at least within the water-filled pores of the gel. The presently preferred DEAE material are Sephadex® A-25 and A-50, with the former being more preferred because of its superior flow characteristics.

Sephadex® and similar materials have hitherto not been used as iodine donors probably because they could not be readily iodinated by ordinary treatments. Generally, iodine donating materials are insoluble iodophors that bind iodine and can readily be iodinated by aqueous iodine solutions. This is not the case with the Sephadex materials which bind iodine weakly or not at all. However, the present inventor has had great success in iodinating Sephadex materials by utilizing the methods he had previously developed to iodinate other organic polymers such as plastics.

It has been found that Sephadex materials can be readily iodinated to levels between 10% and 60% weight iodine/weight Sephadex® by iodine sublimation. At levels below 10% the rate of iodine donation of the end product is generally inadequate. At iodination levels between 10% and 50% the dry Sephadex® material behaves normally as a free flowing powder. At iodination levels of 50–60% and higher the iodinated Sephadex® becomes sticky and difficult to pour dry although it can be handled as an aqueous suspension. At 60% iodine and higher the Sephadex® does not always swell normally in water and, so, is generally not useable. Thus, the optimum level of iodination appears to be between 30 and 40%.

FIG. 1 diagrams a simple procedure for iodinating Sephadex. The first step is to place an aliquot of the dry Sephadex material into a glass or plastic vessel (i.e., a centrifuge tube) that can be sealed air tight. The required amount of dry elemental iodine is then placed into the container and the container sealed. The sealed container is placed on a mixer, for example an "Ferris wheel" mixer, that rotates the container (preferably end over end) in a 37° C. oven. Within about six hours all of the elemental iodine will have been absorbed by the Sephadex. As explained above in reference to Table 1, a higher temperature will accelerate the process by increasing the vapor pressure of the iodine. However, in the above process Sephadex materials aggregate or show other signs of damage at temperatures much above 55° C. Therefore, 37° C. seems a safe and usable temperature. It has been found that inserting a small weight, such as a Teflon-coated magnetic stir bar, can help with the mixing process. Care should be taken to avoid an overly large weight as it may crush the Sephadex and contribute to the formation of "fines." An ordinary glass marble also works admirably, at least for relatively small batches of Sephadex.

Figure 2:
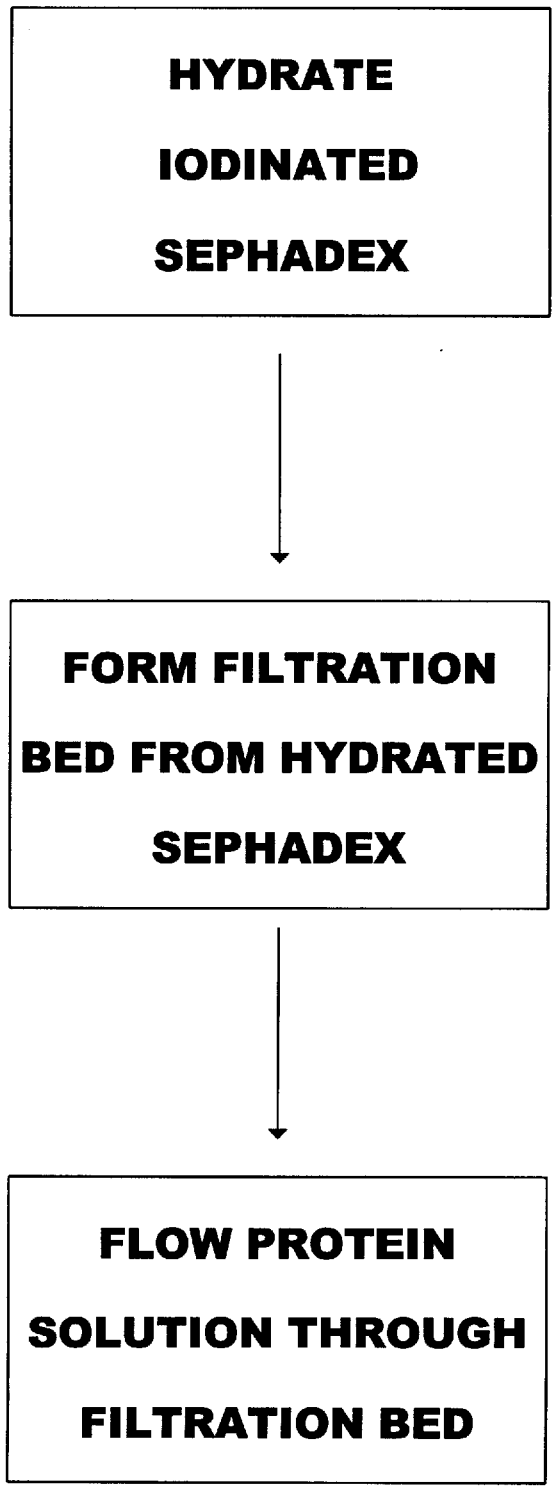
FIG. 2 represents a flow diagram of the process of using the iodinated gel filtration medium to disinfect protein-containing solutions.

The iodinated Sephadex® appears to be stable dry and will keep for an extended period (at least many months) in a well sealed container without losing potency. FIG. 2 diagrams the use of the iodinated Sephadex. The material must be swelled (hydrated) for a few hours prior to use. The polymer may be swelled in plain water, in saline or in appropriate buffers. Care should be taken not to use organic buffers such as histidine-based or imidazole-based buffers because these compounds themselves are readily iodinated, thus exhausting the supply of iodine. Some other organic buffer may be weak iodophors and tend to dissolve an excess amount of iodine from the column. With buffers of this type the column will be prematurely stripped of iodine. It is fairly simple to test a small quantity of iodinated Sephadex® with each new buffer to see if the buffer strips the iodine from the column. If the buffer picks up an iodine color or if the Sephadex® becomes visibly decolorized, the buffer is not suitable. Both phosphate and acetate buffers have proven successful. Since iodination reactions are accelerated at alkaline pH, Sephadex® life can be extended and the iodination reaction controlled by operating the column at a somewhat acid pH such a pH 5.5–6.0 with an acetate buffer.

A relatively small volume of iodinated Sephadex can be used to treat a considerable volume of protein-laden solution. The column configuration (i.e., column width and bed height) should be optimized depending on flow rate and material to be iodinated. In tests using 5% (weight by volume) human IgG about 6 ml of 30% iodine Sephadex was able to treat at least a liter of solution. Iodine donation was affected by both flow rate and column configuration. A thin column (0.7 cm) with a bed height of about 17 cm produced less uniform results than did a thicker (1.6 cm) column with a 3 cm bed height. It appears that an excessively deep bed is more likely to over-iodinate the material because of the longer contact time between the Sephadex and the solution. Over-iodination may strip iodine from part of the column and lead to nonuniform results. Similarly, a higher flow rate (i.e., 6 ml/min versus 2 ml/min) seems to allow more uniform iodination of a larger total volume of protein solution. Obviously, column size, bed volume, flow rate, and protein concentration are variables that can be adjusted to produce the most economical and uniform results.

The goal of using iodinated Sephadex® is to provide an effective virucidal disinfectant. To test the efficacy of the iodinated Sephadex 5% human IgG solution was spiked with virus prior to being treated with the iodinated Sephadex®. Porcine Parvovirus (PPV) was selected as a model for the extremely difficult to inactivate Human Parvovirus B19. The parvoviruses are nonenveloped viruses (i.e., they cannot be inactivated with detergents as can enveloped viruses) with single-stranded DNA as a genetic material. After iodine treatment, the treated material was added to petri plates containing confluent monolayers of tissue culture cells to assay for the presence of active virus.

Two 800 ml portions of 5% IgG (40 g of IgG) either with or without PPV were processed through parallel, identical columns. Each column contained 2 g of 40% iodine DEAE Sephadex A-25 (1.2 g Sephadex®+0.8 g iodine) produced as described above. Flow rates of 6 ml/min were used at 22° C. When the treated solution was tested after incubating for 24 hr at 37° C., all detectable virus has been eliminated. Gel filtration and other tests of the treated IgG indicated that the iodine treatment had resulted in only minimal alteration in the monomer versus dimer content of the IgG. It is anticipated that these minor changes will not effect the end use of the IgG.

Iodinated Sephadex® is a novel and effective manner of disinfecting protein solutions. Surprisingly large amounts of elemental iodine can be introduced into Sephadex® through a sublimation process without altering the normal gel filtration properties of the Sephadex. Extremely recalcitrant viruses like PPV can be effectively killed in protein rich solutions with little or no damage to the protein. It is anticipated that other pathogenic viruses will also be killed under similar situations since PPV is generally regarded as being very difficult to kill.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for producing an iodine donating material for disinfecting protein containing solutions, the method comprising the steps of:

placing a non-hydrated organic polymer gel filtration material into a sealable container;

adding elemental iodine equivalent to at least 10% by weight of said gel filtration material to the container without any solvent;

sealing the container and placing the container on a mixing device which continually agitates the container so as to thoroughly mix the iodine and the gel filtration material; and continuing mixing the gel filtration material so that all of the elemental iodine sublimes and becomes deposited within the gel filtration material yielding gel filtration material that is at least 22% by weight iodine.

2. The method of claim 1, wherein the gel filtration material comprises cross-linked dextrans.

3. The method of claim 2, wherein the cross-linked dextrans are SEPHADEX brand cross-linked dextrans.

4. The method of claim 3, wherein the SEPHADEX® brand cross-linked dextrans is DEAE SEPHADEX brand.

5. The method of claim 1, wherein weight of the elemental iodine is between 22% and 60% weight of the gel filtration material.

6. The method of claim 5, wherein weight of the elemental iodine is between 30% and 50% weight of the gel filtration material.

7. A method for disinfecting protein-containing solutions, the method comprising the steps of:

hydrating gel filtration material by mixing the gel filtration material into an aqueous medium, said gel filtration material containing at least 10% by weight elemental iodine;

pouring the hydrated gel filtration material into a container to produce an iodinating bed of the hydrated gel filtration material; and allowing a protein containing solution to flow through the iodinating bed, whereby elemental iodine held within the gel filtration material transfers to the protein solution destroying any viruses therein.

8. The method of claim 7, wherein the iodinated gel filtration material is iodinated SEPHADEX brand cross-linked dextrans.

9. The method of claim 8, wherein the SEPHADEX brand cross-linked dextrans is DEAE SEPHADEX brand.

10. A material for disinfecting a protein-containing solution, the material comprising a cross-linked organic polymer having properties of a gel filtration medium to which polymer is added elemental iodine equal to at least 22% of the weight of the organic polymer through sublimation of the iodine into the organic polymer with no solvent in a non-hydrated state, at a temperature lower than a temperature that causes decomposition of the organic polymer.

11. A material for disinfecting a protein-containing solution, the material comprising SEPHADEX brand cross-linked dextrans polymer having properties of a gel filtration medium to which polymer is added elemental iodine equal to between 22% and 60% of the weight of the organic polymer through sublimation of the iodine without solvent into the dextrans polymer in a non-hydrated state.

12. A method for disinfecting protein-containing solutions, the method comprising the steps of:

hydrating iodinated anion exchange gel filtration material by mixing the gel filtration material into an aqueous medium, said gel filtration material containing at least 40% by weight elemental iodine;

placing the hydrated gel filtration material into a container to produce an iodinating bed of the hydrated gel filtration material; and allowing a protein containing solution to flow through the iodinating bed, whereby elemental iodine held within the gel filtration material destroys any viruses therein without significantly denaturing protein in the solution.

* * * * *